United States Patent [19]
Amschler

[11] Patent Number: 6,020,340
[45] Date of Patent: Feb. 1, 2000

[54] IMIDAZOPYRIDINES

[75] Inventor: Hermann Amschler, Radolfzell, Germany

[73] Assignee: Byk Gulden Lomberg Chemische Fabrik GmbH, Constance, Germany

[21] Appl. No.: 09/171,918

[22] PCT Filed: May 6, 1997

[86] PCT No.: PCT/EP97/02310

§ 371 Date: Aug. 4, 1998

§ 102(e) Date: Aug. 4, 1998

[87] PCT Pub. No.: WO97/43288

PCT Pub. Date: Nov. 20, 1997

[30] Foreign Application Priority Data

May 15, 1996 [DE] Germany .............................. 196 19 575
May 17, 1996 [EP] European Pat. Off. ............... 96107868

[51] Int. Cl.[7] .......................... A61K 31/44; C07D 471/04
[52] U.S. Cl. .............................. 514/278; 514/303; 546/15; 546/118
[58] Field of Search ...................... 546/15, 118; 514/278, 514/303

[56] References Cited

U.S. PATENT DOCUMENTS 4,963,561  10/1990  Lesher ...................................... 514/303

FOREIGN PATENT DOCUMENTS 079083   5/1983   European Pat. Off. .
96/03399 2/1996   WIPO .

Primary Examiner—Evelyn Mei Huang
Attorney, Agent, or Firm—Jacobson, Price, Holman & Stern PLLC

[57] ABSTRACT

Compounds of formula I (I)

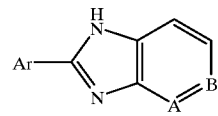

wherein one of A and B is a nitrogen atom and the other is CH, and Ar has one of the meanings stated in the specification, are effective bronchial therapeutics and are also useful for treating dermatoses. These compounds are synthesized and formed into medicament compositions. The compounds and resulting medicament compositions are used for treating airway disorders and dermatoses.

15 Claims, No Drawings

IMIDAZOPYRIDINES

This application is the national phase of PCT/EP07/02310, filed on May 6, 1997.

FIELD OF APPLICATION OF THE INVENTION

The invention relates to novel imidazo[4,5-b]- and imidazo[4,5-c]pyridines, which are used in the pharmaceutical industry for the production of medicaments.

KNOWN TECHNICAL BACKGROUND

European Patent Application EP 22 495 describes 2-(substituted phenyl)imidazo[4,5-b]pyridines as cardiotonics and hypertensive agents. European Patent Application EP 72 926 describes 2-(substituted phenyl)imidazo[4,5-b]- and [4,5-c]pyridines having positive inotropic properties. European Patent Application EP 79 083 describes 2-phenylimidazo-[4,5-]pyridines having vasodilating, positive inotropic and platelet aggregation-inhibiting properties and which do not have an inhibitory action on the myocardial phosphodiesterase. German Patent Application DE 32 24 512 describes, inter alia, 2-phenylimidazo-[4,5-b] pyridines for the treatment of cardiac insufficiency by increasing the contractility of the heart, and for lowering the blood pressure. German Patent Application DE 32 25 386 describes 2-naphthylimidazo-[4,5-b]pyridines having positive inotropic, hypotensive and platelet aggregation-inhibiting properties. German Patent Application DE 23 61 757 describes 2-(substituted phenyl)imidazo[4,5-b] pyridines having hypotensive, positive inotropic, platelet aggregation-inhibiting and bleeding time-prolonging properties.

DESCRIPTION OF THE INVENTION

It has now been found that the novel imidazo[4,5-b]- and imidazo[4,5-c]pyridines described in detail in the following have surprising and particularly advantageous properties.

The invention thus relates to compounds of the formula I (see attached formula sheet), in which A or B is a nitrogen atom (N) and the other letter in each case represents the group CH, Ar represents a heterocycle having the meaning (a) or (b) (see attached formula sheet), where R1 is 1–4C-alkoxy or completely or mainly fluorine-substituted 1–4C-alkoxy, R2 is hydrogen, 1–7C-alkyl, 3–7C-cycloalkyl or 3–7C-cycloalkylmethyl, R3 is hydrogen, 1–7C-alkyl, 3–7C-cycloalkyl or 3–7C-cycloalkylmethyl, or in which R2 and R3, together and including the carbon atom to which both are bonded, represent a 3–7C-cycloalkyl radical, and their tautomeric forms, and the salts of these compounds.

1–4C-Alkoxy is a radical which, beside the oxygen atom, contains a straight-chain or branched alkyl radical having 1 to 4 carbon atoms. Alkyl radicals having 1 to 4 carbon atoms which may be mentioned here, for example, are the butyl, isobutyl, sec-butyl, tert-butyl, propyl, isopropyl, ethyl and methyl radicals.

A completely or mainly fluorine-substituted 1–4C-alkoxy which may be mentioned, for example, is the 1,2,2-trifluoroethoxy, the 2,2,3,3,3-pentafluoropropoxy, the perfluoroethoxy and in particular the 1,1,2,2-tetrafluoroethoxy, the trifluoromethoxy, the 2,2,2-trifluoroethoxy and preferably the difluoromethoxy radical.

1–7C-Alkyl represents straight-chain or branched alkyl radicals having 1 to 7 carbon atoms. Examples which may be mentioned are the heptyl, isoheptyl (2-methylhexyl), hexyl, isohexyl, (2-methylpentyl), neohexyl (2,2-dimethylbutyl), pentyl, isopentyl (3-methylbutyl), neopentyl (2,2-dimethylpropyl), butyl, isobutyl, sec-butyl, tert-butyl, propyl, isopropyl, ethyl and methyl radicals.

3–7C-Cycloalkyl represents the cyclopropyl, cyclobutyl, cyclopentyl, cyclohexyl and cycloheptyl radicals. The 3–5C-cycloalkyl radicals cyclopropyl, cyclobutyl and cyclopentyl may be preferably mentioned.

3–7C-Cycloalkylmethyl represents a methyl radical which is substituted by one of the abovementioned 3–7C-cycloalkyl radicals. The 3–5C-cycloalkylmethyl radicals cyclopropylmethyl, cyclobutylmethyl and cyclopentylmethyl may be preferably mentioned.

Compounds of the formula I to be emphasized are those in which

A or B is a nitrogen atom (N) and the other letter in each case represents the group CH, Ar represents a heterocycle having the meaning (a) or (b), where R1 is 1–2C-alkoxy or completely or mainly fluorine-substituted 1–2C-alkoxy, R2 is hydrogen, 1–7C-alkyl or 3–5C-cycloalkyl and R3 is hydrogen, 1–7C-alkyl or 3–5C-cycloalkyl, or R2 and R3, together and including the carbon atom to which both are bonded, represent a 3–7C-cycloalkyl radical, and their tautomeric forms, and the salts of these compounds.

Preferred compounds of the formula I are those in which

A or B is a nitrogen atom (N) and the other letter in each case represents the group CH, Ar represents a heterocycle having the meaning (a), where R1 is 1–2C-alkoxy or completely or mainly fluorine-substituted 1–2C-alkoxy, R2 is hydrogen, 1–4C-alkyl or 3–5C-cycloalkyl and R3 is hydrogen or 1–4C-alkyl, or R2 and R3, together and including the carbon atom to which both are bonded, represent a cyclopropyl, cyclobutyl or cyclopentyl ring, or Ar represents a heterocycle having the meaning (b), where R1 is 1–2C-alkoxy or completely or mainly fluorine-substituted 1–2C-alkoxy, R2 is 1–4C-alkyl or 3–5C-cycloalkyl and R3 is hydrogen or 1–4C-alkyl, or R2 and R3, together and including the carbon atom to which both are bonded, represent a cyclopropyl, cyclobutyl or cyclopentyl ring, and their tautomeric forms, and the salts of these compounds.

Particularly preferred compounds of the formula I are those in which

A or B is a nitrogen atom (N) and the other letter in each case represents the group CH, Ar represents a heterocycle having the meaning (a), where R1 is difluoromethoxy or methoxy, R2 is 1–4C-alkyl and R3 is 1–4C-alkyl, or R2 and R3, together and including the carbon atom to which both are bonded, represent a cyclopropyl, cyclobutyl or cyclopentyl ring, or Ar represents a heterocycle having the meaning (b), where R1 is difluoromethoxy or methoxy, R2 and R3, together and including the carbon atom to which both are bonded, represent a cyclopropyl, cyclobutyl or cyclopentyl ring, and their tautomeric forms, and the salts of these compounds.

Possible salts for compounds of the formula I, depending on substitution, are all acid addition salts or all salts with bases. Particular mention may be made of the pharmacologically tolerable salts of the inorganic and organic acids customarily used in pharmacy. Those which are suitable are on the one hand water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid, the acids being employed in salt preparation—depending on whether it is a mono- or polybasic acid and depending on which salt is desired—in an equimolar quantitative ratio or one differing therefrom.

On the other hand, salts with bases are also possible. Examples of salts with bases which may be mentioned are alkali metal (lithium, sodium, potassium) or calcium, aluminum, magnesium, titanium, ammonium, meglumine or guanidinium salts, where here also the bases are employed in salt preparation in an equimolar quantitative ratio or one differing therefrom.

Pharmacologically intolerable salts which can be initially obtained, for example, in the preparation of the compounds according to the invention on an industrial scale as process products, are converted into pharmacologically tolerable salts by processes known to the person skilled in the art.

The compounds of the formula I are tautomers and—if the substituents R2 and R3 are not identical—also chiral compounds. The invention therefore includes both the pure tautomers and enantiomers and their mixtures in any mixing ratio, including the racemates. The enantiomers can be separated (see, for example, WO92/08716) in a manner known per se (for example by preparation and separation of appropriate diastereoisomeric compounds).

The invention further relates to a process for the preparation of the compounds of the formula I and their salts. The process comprises condensing carboxylic acids of the formula II (see attached formula sheet), in which Ar has the meaning indicated above, with diaminopyridines of the formula III (see attached formula sheet), in which A and B have the meanings mentioned above, and if desired then converting resulting compounds of the formula I into their salts, or, if desired, then converting resulting salts of the compounds of the formula I into the free compounds.

The condensation is carried out in a manner known per se to the person skilled in the art in the presence of a suitable condensing agent, such as, for example, phosphorus oxychloride, in a suitable inert solvent, e.g. in a chlorinated hydrocarbon such as chloroform, or in a cyclic hydrocarbon such as toluene or xylene, or another inert solvent such as acetonitrile, or without further solvent using an excess of condensing agent, preferably at elevated temperature, in particular at the boiling temperature of the solvent or condensing agent used.

Intermediates of the formulae IVa and/or IVb optionally formed in the condensation (see attached formula sheet), in which the substituents and symbols have the abovementioned meanings, can be isolated. The further internal condensation to give corresponding compounds of the formula I is preferably carried out by treatment with an acid, such as, for example, p-toluenesulfonic acid in a suitable solvent. Water of reaction formed in this process is expediently removed continuously by azeotropic distillation.

For example, the reaction is carried out as described in the following examples or, for example, as described in European Patent Application EP 72 926, in J. Med. Chem. 28 (6) [1985] 717–727 or in Arch. Pharm. 323 (8) [1990]501–505.

The isolation and purification of the substances according to the invention is carried out in a manner known per se, for example by distilling off the solvent in vacuo and recrystallizing the resulting residue from a suitable solvent or subjecting it to one of the customary purification methods, such as, for example, column chromatography on suitable support material.

Salts are obtained by dissolving the free compound in a suitable solvent, e.g. in a chlorinated hydrocarbon, such as methylene chloride or chloroform, or a low-molecular weight aliphatic alcohol (ethanol, isopropanol), which contains the desired acid or base, or to which the desired acid or base is then added. The salts are obtained by filtering, reprecipitating, precipitating with a nonsolvent for the addition salt or by evaporating the solvent. Salts obtained can be converted by basification or by acidification into the free compounds, which in turn can be converted into salts. In this way, pharmacologically nontolerable salts can be converted into pharmacologically tolerable salts.

Carboxylic acids of the formula II in which Ar has the meanings indicated above are accessible from the corresponding compounds of the formula V (see attached formula sheet), in which Z is formyl (CHO) or cyano (CN).

For example, compounds of the formula V in which Z has the meaning of cyano are hydrolyzed with alkali metal hydroxides (if appropriate using hydrogen peroxide), or appropriately substituted compounds of the formula V in which Z has the meaning of formyl are oxidized to the compounds of the formula II (e.g. as described in J. Org. Chem. 1986, 51, 569–571).

Diaminopyridines of the formula III are known or can be prepared in a known manner.

The compounds of the formula V in which Ar represents a heterocycle having the meaning (a) (see attached formula sheet) and Z has the abovementioned meanings are accessible by a cesium fluoride-mediated Claisen rearrangement of the appropriately substituted compounds of the formula VI (see attached formula sheet) (e.g. as described in Chem. Pharm. Bull. 1992, 40(5), 1148–1153 and Chem. Pharm. Bull. 1992, 40(8), 2002–2006). In the compounds of the formula VI, R1, R2 and R3 have the meanings indicated above and Z represents cyano or formyl.

The compounds of the formula V in which Ar represents a heterocycle having the meaning (b) (see attached formula sheet) and Z has the abovementioned meanings are accessible by a Claisen rearrangement of the appropriately substituted compounds of the formula VI (see attached formula sheet) (e.g. as described in J. Med. Chem. 1983, 26(11), 1585 or in Chem. Pharm. Bull. 1992, 40(5), 1148–1153 and literature cited there). In the compounds of the formula VI, R1, R2 and R3 have the meanings indicated above and Z represents cyano or formyl.

The compounds of the formula V in which Ar represents a heterocycle having the meaning (a) or (b) and Z is cyano can be obtained from the appropriately substituted compounds of the formula V in which Z is formyl by reaction with hydroxylamine in formic acid (e.g. as described in Synthesis 1979, 2, 112–113).

The compounds of the formula VI are either known or can be prepared in a manner known to the person skilled in the art, such as described, for example, in Tetrahedron Lett. 1994, 35, 6405–6408.

The following examples serve to illustrate the invention in greater detail without restricting it. Likewise, further compounds of the formula I whose preparation is not explicitly described can be prepared in an analogous manner or in a manner familiar per se to the person skilled in the art using customary process techniques.

In the examples, m.p. represents melting point, b.p. boiling point, h hour(s), RT room temperature, EF empirical formula, MW molecular weight, Calc. calculated. The compounds and their salts mentioned in the examples are a preferred subject of the invention.

EXAMPLES

Final products 1. 2-[7-Methoxy-2-(1-methylethyl)benzofuran-4-yl]imidazo[4,5-b]pyridine 4.6 g of 7-methoxy-2-(1-methylethyl)benzofuran-4-carboxylic acid and 2.2 g of 2,3-diaminopyridine are boiled under reflux for 4 h in 80 ml of phosphorus oxychloride. The mixture is largely evaporated in vacuo, the residue is partitioned between 100 ml of ice water and 500 ml of ethyl acetate and the aqueous phase is rendered alkaline with 50 percent sodium hydroxide solution. The organic phase is separated off, the aqueous phase is extracted a further two times by shaking with ethyl acetate, and the organic phases are combined, dried over ignited calcium carbonate and concentrated in vacuo. The residue is chromatographed on silica gel using a 1:1 mixture of toluene and ethyl acetate. After the evaporation of appropriate fractions, 1.7 g (28.3% of theory) of title compound having the m.p. 242° C. are obtained.

EF: $C_{18}H_{17}N_3O_2$, MW: 307.34

Elemental analysis: Calc.: C, 70.34; H, 5.58; N, 13.67; Found: C, 70.23; H, 5.50; N, 13.58.

Starting from the starting compounds described in the following, the final products described in the following are obtained, by reacting the appropriate carboxylic acids of the formula II with appropriate diaminopyridines of the formula III analogously to Example 1:

2. 2-[7-Difluoromethoxy-2(1-methylethyl)benzofuran-4yl]imidazo[4,5-b]pyridine

M.p.: 236° C.

EF: $C_{18}H_{15}F_2N_3O_2$, MW: 343.32

Elemental analysis: Calc.: C, 62.97; H, 4.40; F, 11.07; N, 12.24; Found: C, 63.07; H, 4.43; F, 11.00; N, 12.08.

3. 2-[8-Methoxy-2,2-tetramethylene-1[2H]chromen-5-yl]imidazo[4,5-b]pyridine

M.p.: 258° C.

EF: $C_{20}H_{19}N_3O_2$, MW: 333.38

Elemental analysis: Calc.: C, 72.05; H, 5.74; N, 12.61; Found: C, 71.88; H, 5.80; N, 12.52.

4. 2-(2Cyclopentyl-7-methoxy-benzofuran-4-yl)imidazo[4,5-c]pyridine

M.p.: 202–204° C.

EF: $C_{20}H_{19}N_3O_2$, MW: 333.39

Elemental analysis: Calc.: C, 72.05; H, 5.74; N, 12.60; Found: C, 72.03; H, 5.81; N, 12.55.

5. 2-[8-Methoxy-2,2-tetramethylene-1[2H]chromen-5-yl]imidazo[4,5-c]pyridine

M.p.: 203–204.5° C.

EF: $C_{20}H_{19}N_3O_2$, MW: 333.38

Elemental analysis: Calc.: C, 72.05; H, 5.74; N, 12.61; Found: C, 71.65; H, 5.84; N, 12.41.

6. 2-[7-Difluoromethoxy-2-(1-methylethyl)benzofuran-4-yl]imidazo[4,5-c]pyridine 1.8 g of N-(3-aminopyrid-4-yl)-7-difluoromethoxy-2-(1-methylethyl)benzofuran-4carboxamide are boiled with 4.0 g of p-toluenesulfonic acid in 50 ml of toluene for 3 h in a water separator. The cooled solution is extracted by shaking with 50 ml of 2 N sodium hydroxide solution, the separated aqueous phase is extracted a further two times with 50 ml of ethyl acetate each time, and the organic phases are combined, dried over ignited potassium carbonate and concentrated in vacuo. The residue is crystallized from ethanol/water. 1.7 g (100% of theory) of the title compound of m.p. 201° C. are obtained.

EF: $C_{18}H_{15}F_2N_3O_2$, MW: 343.32

Elemental analysis: Calc.: C, 62.97; H, 4.40; F, 11.07; N, 12.24; Found: C, 62.76; H, 4.46; F, 11.10; N, 11.92.

Starting from the starting compounds IVa and/or IVb described in the following, the final product described in the following is obtained analogously to Example 6:

7. 2-[7-Methoxy-2-1-methylethyl)benzofuran-4-yl]imidazo[4,5-c]pyridine

M.p.: 226° C.

EF: $C_{18}H_{17}N_3O_2$, MW: 307.34

Elemental analysis: Calc.: C, 70.34; H, 5.58; N, 13.67; Found: C, 70.36; H, 5.61; N, 13.65.

Starting compounds

A. N-3-Aminopyridyl-4)-7-difluoromethoxy-2-(1-methylethyl)benzofuran-4-carboxamide 5.4 g of 7-difluoromethoxy-2-(1-methylethyl)benzofuran-4-carboxylic acid and 2.2 g of 3,4-diaminopyridine are boiled under reflux for 4 h in 80 ml of phosphorus oxychloride. The mixture is largely evaporated in vacuo, the residue is partitioned between 100 ml of ice water and 500 ml of ethyl acetate and the aqueous phase is rendered alkaline with 50 percent sodium hydroxide solution. The organic phase is separated off, the aqueous phase is extracted a further two times by shaking with ethyl acetate, and the organic phases are combined, dried over ignited potassium carbonate and concentrated in vacuo. The residue is chromatographed on silica gel using a 9:1 mixture of ethyl acetate and methanol. After the evaporation of appropriate fractions, 2.0 g (29.4% of theory) of the title compound of m.p. 199° C. are obtained.

In the same manner, starting from an appropriate carboxylic acid of the formula It in which Ar represents a heterocycle having the meaning (a) (see attached formula sheet), the compound described in the following is prepared:

B. N-(3-Aminopyridyl-4)-7-methoxy-2-(1-methylethyl)benzofuran-4-carboxamide

M.p.: 236° C.

C. 7-Difluoromethoxy-2(1-methylethyl)benzofuran-4carboxylic acid

A solution of 0.88 g of sodium chlorite in 5 ml of water is added dropwise to 1.6 g of 7-difluoromethoxy-2-(1-methylethyl)benzofuran-4-carbaldehyde and 0.83 g of amidosulfuric acid, dissolved in 15 ml of glacial acetic acid, such that the internal temperature is kept between 15 and 20° C. The mixture is stirred for a further 1 h and then poured into 150 ml of ice water, and the precipitate formed is filtered off with suction and washed with water until acid-free. For purification, the crude product is dissolved in halfconcentrated, aqueous ammonia, and the aqueous solution is extracted with toluene and acidified with 2 N hydrochloric acid to pH 1–2. The precipitate formed is filtered off with suction, washed with water until acid-free and dried in vacuo: m.p. 169° C.

In a similar manner, starting from an appropriate carbaldehyde of the formula V in which Ar has the abovementioned meanings and Z is formyl, the following compounds are prepared:

D. 7-Methoxy-2-(1-methylethyl)benzofuran-4-carboxylic acid

M.p.: 166° C.

E. 8-Methoxy-2,2-tetramethylene-1[2H]chromene-5-carboxylic acid

M.p.: 181° C.

F. 7-Methoxy-2-cyclopentylbenzofuran-4-carboxylic acid 0.5 g of 7-methoxy-2-cyclopentylbenzofuran-4carbonitrile is heated to reflux for 5 h in a solution of 10 ml of n-butanol, 30 ml of sodium hydroxide solution (50% strength) and 2.5 ml of hydrogen peroxide (30% strength).

The mixture is then diluted with ice water, acidified to pH 1–2 with 2 N hydrochloric acid and the precipitate formed is filtered off with suction, washed with water until acid-free and dried in vacuo: m.p. 170–171° C.

In a similar manner, starting from an appropriate carbonitrile of the formula V in which Ar represents a heterocycle having the meaning (b) and Z is cyano, the following compound is prepared:

G. 8-Methoxy-2,2-tetramethylene-1[2H]chromene-5-carboxylic acid
M.p.: 180° C.

H. 7-Difluoromethoxy-2-(1-methylethyl)benzofuran-4-carbaldehyde 5.5 g of 4-difluoromethoxy-3-(2-methyl-3-butyn-2-yloxy) benzaldehyde are heated to reflux with 7.2 g of cesium fluoride with nitrogen aeration for 12 h in 30 ml of N,N-diethylaniline. The mixture is stirred into 300 ml of 4 N hydrochloric acid after cooling, the resulting emulsion is extracted three times with 50 ml of ethyl acetate, and the organic extracts are combined, dried over ignited potassium carbonate and evaporated in vacuo. The residue is chromatographed on silica gel using toluene. After the evaporation of the appropriate fractions, the title compound is obtained as an oil.

In the same manner, starting from the appropriate benzaldehydes of the formula VI in which Z represents a formyl group, the following compounds are prepared:

H. 7-Methoxy-2-(1-methylethyl)benzofuran-4-carbaldehyde
Oil.

J. 7-Methoxy-2-cyclopentylbenzofuran-4-carbaldehyde
Oil.

In the same manner, starting from the appropriate benzonitriles of the formula VI in which Z represents a cyano group, the following compound is prepared:

K. 7-Methoxy-2-1-methylethyl)benzofuran-4-carbonitrile
Oil.

L. 8-Methoxy-2,2-tetramethylene-1[2H]chromene-5-carbaldehyde 1.9 g of 3-(1-ethynylcyclopentyloxy)-4-methoxybenzaldehyde are heated to reflux under nitrogen aeration for 3 h in 10 ml of N,N-diethylaniline. The mixture is stirred into 50 ml of 4 N hydrochloric acid after cooling, the resulting emulsion is extracted three times with 20 ml of ethyl acetate, and the organic extracts are combined, dried over ignited potassium carbonate and evaporated in vacuo. The residue is chromatographed on silica gel using dichloromethane. After the evaporation of the appropriates fractions, the title compound of m.p. 71.5–73° C. is obtained.

In the same manner, starting from an appropriate benzonitrile of the formula VI in which Z represents a nitrite group, the following compound is prepared:

M. 8-Methoxy-2,2-tetramethylene-1[2H]chromene-5-carbonitrile
M.p. 62° C.

N. 2-Cyclopentyl-7-methoxybenzofuran-4-carbonitrile 27.6 g of 2-cyclopentyl-7-methoxybenzofuran-4-carbaldehyde are heated to reflux for 1.5 h with 11.6 g of hydroxylamine and 19.7 g of sodium formate in 250 ml of formic acid. The cooled solution is stirred in about 1.5 l of a 1:1 mixture of ice water and ethyl acetate, and the organic phase is separated off, dried over ignited potassium carbonate and evaporated in vacuo. The residual oil is sufficiently pure for further processing.

O. 4-Difluoromethoxy-3-(2-methyl-3-butyn-2-yloxy) benzaldehyde

Solution 1:

19.0 g of 2-methyl-3-butyn-2-ol are dissolved under nitrogen aeration in 60 ml of dry acetonitrile, cooled to −5° C. with ice/salt, 22.8 g of 1,8-diazabicyclo[5.4.0]undec-7-en (DBU) are added, the mixture is stirred at −5° C. for 10 min. and 24.4 g of trifluoroacetic anhydride are then added dropwise such that the temperature of the solution is kept below 0° C. After addition is complete, the solution is stirred at −5° to −2° C. for a further 30 min.

Solution 2:

18.1 g of 4-difluoromethoxy-3-hydroxybenzaldehyde are dissolved under nitrogen aeration in 60 ml of dry acetonitrile, cooled to −5° C. with ice/salt, 0.01 g of copper (I) chloride and 19.8 g of DBU are added and the mixture is stirred for a further 30 min. at −5° C.

Solution 1 is now added dropwise to Solution 2 with stirring at −5° C. in the course of 40 min. and the mixture is stirred for 5 h at 0° C. The mixture is then evaporated in vacuo, the residue is taken up in 100 ml of water and the mixture is extracted three times with 200 ml of toluene each time. The combined toluene extracts are washed successively with three times 50 ml of 1 N hydrochloric acid, two times 50 ml of 1 N sodium hydroxide solution, 50 ml of saturated sodium bicarbonate solution and finally with 50 ml of saturated sodium chloride solution, dried over ignited magnesium sulfate, concentrated in vacuo and chromatographed on silica gel using a mixture of cyclohexane/ethanol (97:3). After evaporation of the appropriate fractions, 4-difluoromethoxy-3-(2-methyl-3-butyn-2-yloxy) benzaldehyde is obtained as an oil.

In the same manner, corresponding to example O., 3-hydroxy-4-methoxybenzaldehyde is reacted with appropriate 1-ethynyl alcohols:

P. 3-(2-Methyl-3-butyn-2-yloxy)-4-methoxybenzaldehyde
Oil.

Q. 3-(1-Ethynylcyclopentyloxy)-4-methoxybenzaldehyde
M.p. 91.5–93° C.

In the same manner, corresponding to example O., the following benzonitriles of the formula VI in which Z represents a cyano group are prepared from 3-hydroxy-4-methoxybenzonitrile:

R. 3-(1,1-Dimethylprop-2-in-1-yloxy)-4-methoxybenzonitrile
M.p. 103° C.

S. 3-(1-Ethynylcyclopentyloxy)-4-methoxybenzonitrile
M.p. 67° C.

Commercial Utility

The compounds according to the invention have useful pharmacological properties which make them commercially utilizable. As selective cyclic nucleotide phosphodiesterase (PDE) inhibitors (namely of type IV), they are suitable on the one hand as bronchial therapeutics (for the treatment of airway obstructions on account of their dilating but also on account of their respiratory rate- or respiratory drive-increasing action) and for the elimination of erectile dysfunction on account of the vasodilating action, but on the other hand especially for the treatment of disorders, in particular of inflammatory nature. e.g. of the airways (asthma prophylaxis), of the skin, of the intestine, of the eyes and of the joints, which are mediated by mediators such as histamine, PAF (platelet-activating factor), arachidonic acid derivatives such as leukotrienes and prostaglandins, cytokines, interleukins, chemokines, alpha-, beta- and gamma-interferon, tumor necrosis factor (TNF) or oxygen radicals and proteases. In this context, the compounds according to the invention are distinguished by a low toxicity, a good enteral absorption (high bioavailability), a large therapeutic width and the absence of appreciable side effects.

On account of their PDE-inhibiting properties, the compounds according to the invention can be employed in human and veterinary medicine as therapeutics, where they can be used, for example, for the treatment and prophylaxis of the following illnesses: acute and chronic (in particular inflammatory and allergen-induced) airway disorders of varying origins (bronchitis, allergic bronchitis, bronchial asthma); dermatoses (especially of proliferative, inflammatory and allergic nature) such as, for example, psoriasis (vulgaris), toxic and allergic contact eczema, atopic eczema, seborrheic eczema, lichen simplex, sunburn, pruritus in the anogenital region, alopecia areata, hypertrophic scars, discoid lupus erythematosus, follicular and wide-area pyodermias, endogenous and exogenous acne, acne rosacea, and other proliferative, inflammatory and allergic skin disorders; disorders which are based on an excessive release of TNF and leukotrienes, e.g. disorders of the arthritis type (rheumatoid arthritis, rheumatoid spondylitis, osteoarthritis and other arthritic conditions), disorders of the immune system (AIDS, multiple sclerosis), shock symptoms [septic shock, endotoxin shock, gram-negative sepsis, toxic shock syndrome and ARDS (adult respiratory distress syndrome)], and generalized inflammations in the gastrointestinal region (Crohn's disease and ulcerative colitis); disorders which are based on allergic and/or chronic, faulty immunological reactions in the region of the upper airways (pharynx, nose) and the adjacent regions (paranasal sinuses, eyes), such as, for example, allergic rhinitis/sinusitis, chronic rhinitis/sinusitis, allergic conjunctivitis and nasal polyps; but also disorders of the heart which can be treated by PDE inhibitors, such as, for example, cardiac insufficiency, or disorders which can be treated on account of the tissue-relaxing action of the POE inhibitors, such as, for example, erectile dysfunction or colics of the kidneys and of the ureters in connection with kidney stones.

The invention further relates to a process for the treatment of mammals, including humans, which are suffering from one of the abovementioned diseases. The process comprises administering to the sick mammal a therapeutically active and pharmacologically tolerable amount of one or more of the compounds according to the invention.

The invention further relates to the compounds according to the invention for use in the treatment and/or prophylaxis of the diseases mentioned.

The invention likewise relates to the use of the compounds according to the invention for the production of medicaments which are employed for the treatment and/or prophylaxis of the diseases mentioned.

The invention furthermore relates to medicaments for the treatment and/or prophylaxis of the diseases mentioned, which contain one or more of the compounds according to the invention.

The medicaments are prepared by processes which are known per se and familiar to the person skilled in the art. As medicaments, the compounds according to the invention (=active compounds) are used either as such, or preferably in combination with suitable pharmaceutical auxiliaries, e.g. in the form of tablets, coated tablets, capsules, suppositories, plasters, emulsions, suspensions, gels or solutions, the active compound content advantageously being between 0.1 and 95%.

The person skilled in the art is familiar on account of his expert knowledge with the auxiliaries which are suitable for the desired pharmaceutical formulations. Beside solvents, gel-forming agents, ointment bases and other active compound excipients, it is possible to use, for example, antioxidants, dispersants, emulsifiers, preservatives, solubilizers or permeation promoters.

For the treatment of disorders of the respiratory tract, the compounds according to the invention are preferably also administered by inhalation. To this end, these are either administered directly as powders (preferably in micronized form) or by atomizing solutions or suspensions which contain them. With respect to the preparations and administration forms, reference is made, for example, to the details in European Patent 163 965.

For the treatment of dermatoses, the administration of the compounds according to the invention takes place, in particular, in the form of those medicaments which are suitable for topical application. For the production of the medicaments, the compounds according to the invention (=active compounds) are preferably mixed with suitable pharmaceutical auxiliaries and processed further to give suitable pharmaceutical formulations. Suitable pharmaceutical formulations which may be mentioned are, for example, powders, emulsions, suspensions, sprays, oils, ointments, fatty ointments, creams, pastes, gels or solutions.

The medicaments according to the invention are prepared by methods known per se. The dosage of the active compounds is carried out in the order of magnitude customary for PDE inhibitors. Thus topical application forms (such as, for example, ointments) for the treatment of dermatoses contain the active compounds in a concentration of, for example, 0.1–99%. The dose for administration by inhalation is customarily between 0.01 and 0.5 mg/kg. The customary dose in the case of systemic therapy is between 0.05 and 2 mg per day.

Biological Investigations

In the investigation of PDE IV inhibition at the cellular level, the activation of inflammatory cells is ascribed particular importance. An example which may be mentioned is the FMLP (N-formyl-methionyl-leucyl-phenylalanine)-induced superoxide production of neutrophilic granulocytes, which can be measured as luminol-potentiated chemoluminescence. [Mc Phail L C, Strum S L, Leone P A and Sozzani S. The neutrophil respiratory burst mechanism. In "Immunology Series" 1992, 57, 47–76; ed. Coffey R G (Marcel Decker, Inc., New York-Basle-Hong Kong)].

Substances which inhibit the chemoluminescence and the cytokine secretion and the secretion of proinflammatory mediators of inflammatory cells, in particular neutrophilic and eosinophilic granulocytes, are those which inhibit PDE IV. This isoenzyme of the phosphodiesterase families is particularly represented in granulocytes. Its inhibition leads to the raising of the intracellular cyclic AMP concentration and thus to the inhibition of cellular activation. PDE IV inhibition by the substances according to the invention is thus a central indicator of the suppression of inflammatory processes. (Giembycz M A, Could isoenzyme-selective phosphodiesterase inhibitors render bronchodilatory therapy redundant in the treatment of bronchial asthma?. Biochem Pharmacol 1992, 43, 2041–2051; Torphy T J et al., Phosphodiesterase inhibitors: new opportunities for treatment of asthma. Thorax 1991, 46, 512–523; Schudt C et al., Zardaverine: a cyclic AMP PDE III/IV inhibitor. In "New Drugs for Asthma Therapy", 379–402, Birkhäuser Verlag Basle 1991; Schudt C et al., Influence of selective phosphodiesterase inhibitors on human neutrophil functions and levels of cAMP and $Ca_i$. Naunyn-Schmiedebergs Arch Pharmacol 1991, 344, 682–690; Nielson C P et al., Effects of selective phosphodiesterase inhibitors on polymorphonuclear leucocyte respiratory burst. J Allergy Clin Immunol 1990, 86, 801–808; Schade et al., The specific type III and IV phosphodiesterase inhibitor zardaverine suppress formation of tumor necrosis factor by macrophages. European Journal of Pharmacology 1993, 230, 9–14).

1. Inhibition of PDE IV activity

Methodology

The activity test was carried out according to the method of Bauer and Schwabe, which was adapted to microtiter plates (Naunyn-Schmiedeberg's Arch. Pharmacol. 1980 311, 193–198). Here the PDE reaction takes place in the first step. In a second step, the 5'-nucleotide formed is cleaved to the uncharged nucleoside by a 5'-nucleotidase of the snake venom of *Ophiophagus hannah* (king cobras. In the third step, the nucleoside is separated from the remaining charged substrate on ion-exchange columns. The columns are eluted with 2 ml of 30 mM ammonium formate (pH 6.0) directly into minivials to which is additionally added 2 ml of scintillator fluid for counting.

The inhibitory values determined for the compounds according to the invention can be seen from the following table A, in which the numbers of the compounds correspond to the numbers of the examples.

TABLE A

Inhibition of PDE IV activity

| Compound | $-\log IC_{50}$ |
|---|---|
| 1 | 7.41 |
| 2 | 8.14 |
| 3 | 5.83 |
| 4 | 7.74 |
| 5 | 6.76 |
| 6 | 8.38 |
| 7 | 8.09 |

(I)

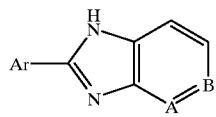

(a)

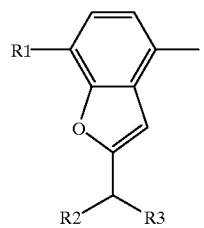

(b)

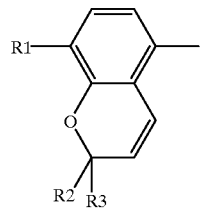

(II)

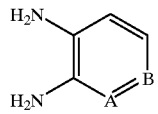

Ar—COOH (III)

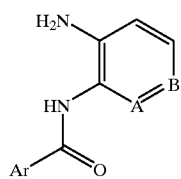

(IVa)

-continued (IVb)

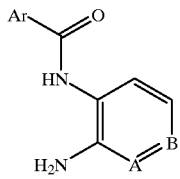

(V)

Ar—Z (VI)

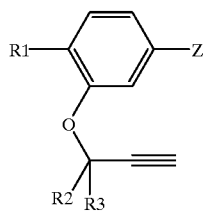

I claim:
1. A compound of the formula I

(I)

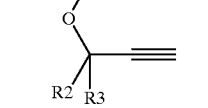

in which
  A or B is a nitrogen atom (N) and the other letter in each case represents the group CH,
  Ar represents a heterocycle having the meaning (a) or (b)

(a)

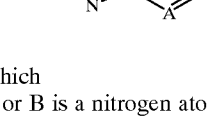

(b)

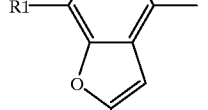

where
  R1 is 1–4C-alkoxy or completely or mainly fluorine-substituted 1–4C-alkoxy,
  R2 is hydrogen, 1–7C-alkyl, 3–7C-cycloalkyl or 3–7C-cycloalkylmethyl,
  R3 is hydrogen, 1–7C-alkyl, 3–7C-cycloalkyl or 3–7C-cycloalkylmethyl,
or in which
  R2 and R3, together with the carbon atom to which both are bonded, represent a 3–7C-cycloalkyl radical, or a tautomeric form, or a salt thereof.

2. A compound of the formula I as claimed in claim 1, in which

A or B is a nitrogen atom (N) and the other letter in each case represents the group CH, Ar represents a heterocycle having the meaning (a) or (b), where R1 is 1–2C-alkoxy or completely or mainly fluorine-substituted 1–2C-alkoxy, R2 is hydrogen, 1–7C-alkyl or 3–5C-cycloalkyl and R3 is hydrogen, 1–7C-alkyl or 3–5C-cycloalkyl, or R2 and R3, together with the carbon atom to which both are bonded, represent a 3–7c-cycloalkyl radical, or a tautomeric form, or a salt thereof.

3. A compound of the formula I as claimed in claim 1, in which

A or B is a nitrogen atom (N) and the other letter in each case represents the group CH, Ar represents a heterocycle having the meaning (a), where R1 is 1–2C-alkoxy or completely or mainly fluorine-substituted 1–2C-alkoxy, R2 is hydrogen, 1–4C-alkyl or 3–5C-cycloalkyl and R3 is hydrogen or 1–4C-alkyl, or R2 and R3, together with the carbon atom to which both are bonded, represent a cyclopropyl, cyclobutyl or cyclopentyl ring, or Ar represents a heterocycle having the meaning (b), where R1 is 1–2C-alkoxy or completely or mainly fluorine-substituted 1–2C-alkoxy, R2 is 1–4C-alkyl or 3–5C-cycloalkyl and R3 is hydrogen or 1–4C-alkyl, or R2 and R3, together with the carbon atom to which both are bonded, represent a cyclopropyl, cyclobutyl or cyclopentyl ring, or a tautomeric form, or a salt thereof.

4. A compound of the formula I as claimed in claim 1, in which

A or B is a nitrogen atom (N) and the other letter in each case represents the group CH, Ar represents a heterocycle having the meaning (a), where R1 is difluoromethoxy or methoxy, R2 is 1–4C-alkyl and R3 is 1–4C-alkyl, or R2 and R3, together with the carbon atom to which both are bonded, represent a cyclopropyl, cyclobutyl or cyclopentyl ring, or Ar represents a heterocycle having the meaning (b), where R1 is difluoromethoxy or methoxy, R2 and R3, together with the carbon atom to which both are bonded, represent a cyclopropyl, cyclobutyl or cyclopentyl ring, or a tautomeric form, or a salt thereof.

5. A process for the preparation of a compound of formula I as claimed in claim 1 or a salt thereof, which comprises condensing a compound of formula II, in which Ar has the meanings indicated in claim 1, with diaminopyridines of the formula III, in which A and B have the meanings indicated in claim 1

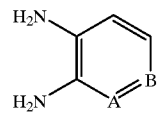

and optionally converting the resulting compound of formula I into its salt, or optionally converting the resulting salt of the compound of formula I into the free compound.

6. A compound of formula I as claimed in claim 1 wherein A is a nitrogen atom.

7. A compound of formula I as claimed in claim 6 wherein Ar represents a heterocycle having the meaning (a).

8. A compound of formula I as claimed in claim 6 wherein Ar represents a heterocycle having the meaning (b).

9. A compound of formula I as claimed in claim 1 wherein A represents the group CH.

10. A compound of formula I as claimed in claim 9 wherein Ar represents a heterocycle having the meaning (a).

11. A compound of formula I as claimed in claim 9 wherein Ar represents a heterocycle having the meaning (b).

12. A medicament composition comprising an effective amount of a) a compound as claimed in claim 1, a tautomer thereof or a pharmaceutically-acceptable salt thereof and b) a pharmaceutically-acceptable carrier therefor.

13. A method of treating a subject afflicted with an amenable airway disorder or an amenable dermatosis which comprises administering to the subject in need thereof an effective amount of a compound of claim 1, a tautomer thereof or a pharmaceutically-acceptable salt thereof.

14. A medicament composition for treating an airway disorder comprising an effective amount of a compound as claimed in claim 1, a tautomer thereof or a pharmaceutically-acceptable salt thereof and a pharmaceutically-acceptable carrier therefor.

15. A medicament composition for treating a dermatosis comprising an effective amount of a compound as claimed in claim 1, a tautomer thereof or a pharmaceutically-acceptable salt thereof and a pharmaceutically-acceptable carrier therefor.

* * * * *

UNITED STATES PATENT AND TRADEMARK OFFICE
CERTIFICATE OF CORRECTION

PATENT NO. : 6,020,340
DATED : February 1, 2000
INVENTOR(S) : Hermann AMSCHLER

It is certified that error appears in the above-identified patent and that said Letters Patent is hereby corrected as shown below:

Column 13, line 14, "3-7c-cycloalkyl" should read --3-7C-cycloalkyl--.
Column 14, line 11, (claim 5, line 6) "claim 1" should read --claim 1      Ar-COOH      (II)--;

line 15, (claim 5, line 7) "  " should read

-- 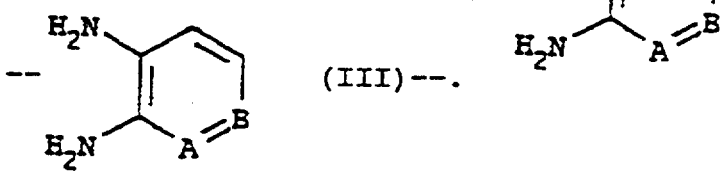     (III)--.

Signed and Sealed this

Twentieth Day of February, 2001

Attest:

NICHOLAS P. GODICI

Attesting Officer    Acting Director of the United States Patent and Trademark Office